(12) United States Patent
Ohashi et al.

(10) Patent No.: US 6,187,995 B1
(45) Date of Patent: Feb. 13, 2001

(54) **METHOD FOR PRODUCING DISEASE RESISTANT PLANT WITH THIONIN GENE FROM *AVENA SATIVA***

(75) Inventors: Yuko Ohashi; Ichiro Mitsuhara; Masahiro Ohshima; Masashi Ugaki; Hirohiko Hirochika, all of Tsukuba; Ryoso Honkura, Natori; Takayoshi Iwai, Natori; Shigeo Nakamura, Natori, all of (JP)

(73) Assignee: Director General of National Institute of Agrobiological Resources, Ministry of Agriculture, Forestry and Fisheries, Ibaragi (JP)

(*) Notice: Under 35 U.S.C. 154(b), the term of this patent shall be extended for 0 days.

(21) Appl. No.: 09/148,802

(22) Filed: Sep. 4, 1998

(30) Foreign Application Priority Data

Sep. 8, 1997 (JP) .................................... 9-243299

(51) Int. Cl.⁷ .................................................. C12N 15/82
(52) U.S. Cl. ........................................ 800/279; 435/320.1
(58) Field of Search .............................. 435/69.1, 320.1, 435/419, 468; 536/23.6; 800/279, 301, 317, 320

(56) References Cited

FOREIGN PATENT DOCUMENTS

| 0 448 511 A1 | 3/1991 | (EP) | A01N/63/00 |
|---|---|---|---|
| 08266279 | 10/1996 | (JP) | C12N/15/09 |
| WO 92/20801 | 11/1992 | (WO) | C12N/15/29 |
| WO 93/04586 | 3/1993 | (WO) | A01N/63/00 |
| WO 94/16078 | 7/1994 | (WO) | C12N/15/29 |

OTHER PUBLICATIONS

Carmona, M., et al. Expression of the a–thionin gene from barley in tobacco conifers enhanced resistance to bacterial pathogens, *The Plant Journal*, 3(3), 457–462 (1993).

Epple, P., et al., "Overexpression of an Endogenous Thionin Enhances Resistance of *Arabidopsis* Against *Fusarium oxysporum*," *The Plant Cell*, vol. 9, 509–520 (1997).

Broekaert, W., et al., "Antimicrobial Peptides from Plants," *Critical Reviews in Plant Sciences*, 16(3): 297–323 (1997).

Holtorf, S., et al. "Specific and different expression patterns of two members of the leaf thionin multigene family of barley in transgenic tabacco," *Plant Science*, 111:27–37 (1995).

Holtorf, S., et al., "High–level expression of a viscotoxin in *Arabidopsis thaliana* gives enhanced resistance against *Plasmodiophora brassicae*," *Plant Molecular Biology* 36:673–680 (1998).

*Primary Examiner*—Amy J. Nelson
(74) *Attorney, Agent, or Firm*—Townsend and Townsend and Crew LLP (57) ABSTRACT

A plant exhibiting resistance to at least one disease is provided. The plant includes an expression cassette including a thionin gene from *Avena sativa*, which is capable of expressing the thionin protein. A method for producing the plant is also provided. The method includes the steps of constructing an expression vector containing an expression cassette including a thionin from *Avena sativa* gene, which is capable of expressing the thionin protein, transforming a plant cell with the expression vector, and regenerating a plant from the transformed plant cell. The plant exhibits resistance to at least one disease such as a disease caused by a plant pathogenic bacterium (e.g., a bacterium causing bacterial leaf blight of rice or a bacterium causing bacterial seedling blight of rice) or a plant pathogenic filamentous fungus (e.g., a fungus causing late blight of potato). A seed obtained from the above disease resistant plant is also provided.

4 Claims, 5 Drawing Sheets

(3 of 5 Drawing Sheet(s) Filed in Color)

FIG. 1.

UPPER LEAF: TRANSGENIC RICE LINE 2-1
LOWER LEAF: WILD TYPE RICE (CV. CHIYOHONAMI)

METHOD FOR PRODUCING DISEASE RESISTANT PLANT WITH THIONIN GENE FROM *AVENA SATIVA*

BACKGROUND OF THE INVENTION

1. Field of the Invention

The present invention relates to a transgenic plant which exhibits resistance to at least one disease. In particular, the present invention relates to a transgenic plant which comprises an expression cassette including a thionin gene and being capable of expressing the thionin gene, and which exhibits resistance to at least one disease.

2. Description of the Related Art

In the field of agricultural production, there has been a general desire for stable production of high quality plants and reduction of dependency on agricultural chemicals. Accordingly, plant species exhibiting resistance to pests and pathogenic microbes have been vigorously improved, bred, and developed, by utilizing useful plant biotechnology techniques, e.g., plant cell fusion techniques and recombinant DNA techniques.

In fact, a transgenic plant exhibiting resistance to herbicides (Japanese Laid-open Publication No. 2-186925), a transgenic plant exhibiting resistance to viruses (Japanese Laid-open Publication No. 4-330233), and a transgenic plant exhibiting resistance to pests (Japanese Laid-open Publication No. 3-247220) have already been produced by employing recombinant DNA techniques.

Furthermore, several kinds of transgenic plants which exhibit resistance to plant pathogenic microbes have been produced, e.g., a transgenic plant which exhibits resistance to pathogenic filamentous fungi by the introduction of a gene encoding an enzyme which inactivates the toxins produced by pathogenic filamentous fungi (Anne S. Ponstein et. al., Plant Physiology, 104: 109–118, 1994), and a transgenic plant which exhibits resistance to at least one pathogenic microbe by the introduction of a gene encoding an antimicrobial protein from an insect (Japanese Laid-Open Publication No. 7-250685).

The inventors isolated from leaves of *Avena sativa* a novel thionin, which is an antimicrobial protein, sequenced a gene encoding the thionin by a known method, and attempted transformation of a tobacco plant using the thionin gene (Japanese Laid-open Publication No. 8-266279). A transformed, redifferentiated tobacco plant has been obtained through this attempt.

However, it is not guaranteed that all transgenic plants will become practical and useful plants exhibiting high disease resistance because factors such as the species of the plant, transformation methods, expressed amounts and expression sites of the introduced genes, and influences of the gene products on the plant may vary the disease resistance or impede growth. Furthermore, it is known that it depends on each situation whether or not the acquired disease resistance will be stably passed down to progenies. For these reasons, it has been desired to produce a practical and useful plant exhibiting high disease resistance.

SUMMARY OF THE INVENTION

An object of the present invention is to produce a plant which comprises an expression cassette including a thionin gene and being capable of expressing the thionin gene, thereby providing a plant exhibiting high resistance to at least one disease. Another object of the present invention is to provide a plant and a seed which allow such properties to be stably retained in progenies. Still another object of the present invention is to provide a method for obtaining the aforementioned plant exhibiting high resistance.

The plant of the present invention is a plant exhibiting resistance to at least one disease, the plant comprising an expression cassette including a thionin gene, the expression cassette being capable of expressing the thionin gene.

The method for producing a disease resistant plant of the present invention is a method comprising the steps of constructing an expression vector containing an expression cassette including a thionin gene, the expression cassette being capable of expressing the thionin gene; transforming a plant cell with the expression vector; and regenerating a plant from the transformed plant cell.

In a preferred embodiment of the present invention, the thionin is derived from a leaf of *Avena sativa*.

In a preferred embodiment of the present invention, the disease resistant plant is a plant of Monocotyledoneae or Dicotyledoneae.

In a preferred embodiment of the present invention, the disease resistant plant is a plant of Poaceae or a plant of Solanaceae.

In a preferred embodiment of the present invention, the disease associated with the disease resistant plant is a disease caused by a plant pathogenic microbe, for example, a disease caused by a plant pathogenic bacterium (e.g., a bacterium causing bacterial leaf blight of rice or a bacterium causing bacterial seedling blight of rice) or a plant pathogenic filamentous fungus (e.g., a fungus causing late blight of potato).

The present invention also comprises a seed obtained from the disease resistant plant.

Thus, the invention described herein makes possible the advantages of (1) producing a plant which comprises an expression cassette including a thionin gene and being capable of expressing the thionin gene, thereby providing a plant exhibiting high resistance to at least one disease; (2) providing a plant and a seed which allow such properties to be stably retained in progenies; and (3) providing a method for obtaining the aforementioned plant exhibiting high disease resistance.

These and other advantages of the present invention will become apparent to those skilled in the art upon reading and understanding the following detailed description with reference to the accompanying figures.

DESCRIPTION OF THE PREFERRED EMBODIMENTS

First, the definitions of the terms used herein will be explained in order to facilitate understanding of the present invention.

The term "disease" as used herein refers to a disease caused by a plant pathogenic microbe including a plant pathogenic bacterium or a pathogenic filamentous fungus. Examples of diseases caused by plant pathogenic bacteria include: bacterial leaf blight of rice, bacterial seedling blight of rice, bacterial seedling rot of rice, hollow stalk of tobacco, and wild-fire of tobacco, as well as soft rots, bacterial spots, and bacterial wilts of vegetables. Examples of diseases caused by pathogenic filamentous fungi include: blast of rice, sheath blight of rice, seed and seedling rot of rice, damping off of rice, bakanae disease, downy mildew of rice, brown spot of rice, rust of wheat, barley, rye, oat or the like, powdery mildew of wheat, barley, rye, oat or the like, late blight of potato, black shank Waterhouse of tobacco, gray mold of tobacco, damping off of tobacco, rust of grass, take-all, snow blight, lemics of vegetables, downey mildew, powdery mildew, anthracnose, seedling blight, clubroot, wilt of carnation, and rust of chrysanthemum. The diseases against which the present invention is particularly useful in providing resistance are bacterial leaf blight of rice, bacterial seedling blight of rice and late blight of potato.

The term "thionin" as used herein refers to a basic protein which has various pharmacological actions such as antimicrobial actions and hypotensive actions, and which is stable against acids and heat. It is generally known that thionin is a protein which is derived from plants (e.g., wheat, barley, rye, oat, and *Avena sativa*), e.g., a cysteine-rich protein consisting of 46 amino acid residues and having a molecular weight of about 5 kilo dalton (kDa). The term "thionin" as used herein also encompasses any protein in which at least one amino acid is added, deleted, or substituted and which retains the aforementioned properties. Preferably, "thionin" refers to the thionin derived from the leaves of *Avena sativa* in the present invention.

The term "transgenic plant" as used herein refers to a plant having an externally introduced gene and being capable of stably or transiently expressing the gene to generate a gene product (e.g., a polypeptide such as an enzyme) having a specific biological function. The expression may be constitutive or inducible (i.e., in response to a specific stimulation, e.g., temperature and/or an agent). The gene to be introduced is derived from a plant to be transformed, a plant which belongs to the same species as or different species from the plant to be transformed, or another species of organism (e.g., animals such as insects, or microbes). Genes which are reconstructed by combining portions of such genes together are also encompassed as the gene to be introduced, as long as the gene product (e.g., enzyme) retains its biological function.

The term "gene" as used herein refers to a polymer in which nucleotides encoding the amino acids constituting a polypeptide (e.g., enzyme) are joined into a linear structure with directionality. The "gene" may be single-stranded (e.g., RNA) or double-stranded (e.g., DNA). DNA may be, for example, cDNA which is enzymatically prepared from a transcribed RNA (mRNA), genomic DNA from chromosomes, or chemically synthesized DNA. Such genes may include a promoter region for regulating the transcription of a coding region, an enhancer region affecting the promoter region, and other regulatory regions (e.g., a terminator and a poly A region) as well as intron or the like, in addition to a sequence corresponding to a coding region or a translational region encoding a polypeptide (e.g., enzyme). It is known in the art that modifications to these genes, e.g., addition, deletion, substitution, may be performed as long as the modified genes retain the activities of the aforementioned regions.

The term "expression cassette" as used herein refers to a DNA fragment in which a gene encoding a protein (e.g., thionin) and various regulatory elements (e.g., promoters and enhancers) for regulating its expression are linked together so as to be operable in a host cell.

The term "vector" as used herein refers to a DNA for transferring the aforementioned expression cassette into a host cell. It is known in the art that the type of such a vector and the kinds of regulatory elements to be used can be varied in accordance with each host cell. A preferred type of the vector is a plasmid vector, and is generally a vector capable of transferring the aforementioned expression cassette into a microbe, an animal cell, or a plant cell. Those which are capable of transferring the aforementioned expression cassette into a plant cell are especially preferable.

Hereinafter, the present invention will be described in detail. Unless otherwise specified, the present invention can be practiced by using known techniques in the field of molecular-biology, biochemistry, genetics, genetic engineering, and/or plant breeding.

The plant to be transformed by the method of the present invention may be a plant of either Monocotyledoneae or Dicotyledoneae. Preferable plants of Monocotyledoneae in the present invention include plants of Poaceae. Examples of the plants of Poaceae include plants of Phyllostachys, Sasa, Sasamorpha, Pleioblastus, Oryza, Poa, Glyceria, Melica, Avena, Agrostis, Bromus, Agropyron, Hordeum, Triticum, Aegilopus, Secale, Phragmites, Eragrostis, Eleusine, Calamaglostis, Zoysia, Panicum, Echinochloa, Setaria, Digitaria, Saccharum, Miscanthus, Imperata, Sorghum, Coix, Zea, and the like. A plant of Oryza is especially preferable. Preferable plants of Dicotyledoneae in the present invention include plants of Solanaceae. Examples of the plants of Solanaceae include plants of Lycium, Scopolia, Physalis, Solanum, Lycopersicon, Capsicum, Nicotiana, Datura, and Petunia. A plant of Nicotiana is especially preferable.

The thionin gene to be used in the present invention may be a gene encoding a thionin which is derived from the endosperms or leaves of, for example, wheat, barley, rye, oat, *Avena sativa* and the like. Alternatively, a gene encoding a thionin which is a protein similar to the thionin from wheat or the like, e.g,. a gene encoding a viscotoxin from mistletoe, a gene encoding a crambin from oilseeds of *Crambe abyssinica*, or a gene encoding a thionin-like protein from the leaves and berries of *Pyrularia pubera* (a parasitic plant of Santalaceae) (Wada and Ozaki, Plant Cell Technology, 3(3): 200–207, 1991), may be used. In the present invention, a thionin gene from the leaves of *Avena sativa* is preferably used.

The thionin genes specifically mentioned above have been isolated, and the nucleotide sequences thereof are known. The nucleotide sequences are registered in a gene sequence registration institution such as GenBank™. Those skilled in the art can obtain the nucleotide sequences of thionin genes by conducting a search on gene sequence registration institutions or various databases (e.g., DNASIS™) which are based on the sequences registered in such gene sequence registration institutions.

A thionin gene useful in the present invention can be directly isolated from various plants based on a known nucleotide sequence, by using a method known to those skilled in the art. Alternatively, a thionin gene which has already been isolated and cloned into a vector can be used. Alternatively, a thionin gene which has been chemically synthesized based on a known nucleotide sequence can be used.

In short, the isolation of thionin genes from various plants can be performed, for example, by isolating mRNA from the thionin-expressing cells of the plant, constructing a gene (CDNA) library from the isolated mRNA, and screening the gene library by a hybridization method. For the hybridization, a polynucleotide which has been chemically synthesized based on a known nucleotide sequence or the full-length or a fragment of an already cloned thionin gene can be used as a hybridization probe. Portions of these operations can be performed by using various commercially available kits intended for the respective operation steps. The conditions and procedure for such a series of operations are described in standard experimental manuals in the art, e.g., Molecular Cloning A Laboratory Manual 2nd Edition (Sambrook, J. et al.(Ed.), Cold Spring Harbor Laboratory Press, 1989) and Current Protocols in Molecular Biology (Ausubel, F. M. et al.(Ed.), John Wiley & Sons, 1987), or the instruction manual attached to each kit.

A portion or region of the sequence of the thionin gene thus obtained may be modified in order to alter its activity or specificity or facilitate the subsequent gene recombining operations as necessary. Such modification can be performed by methods well-known to those skilled in the art, e.g., site-directed mutagenesis or polymerase chain reaction (PCR). It would be appreciated by those skilled in the art that such modification of nucleotide sequences results in the change of one or more amino acid(s) or region(s) of amino acid sequence. These conditions are within the knowledge of those skilled in the art. These standard methods are described in the aforementioned experimental manuals.

An expression cassette for efficiently expressing a thionin gene within plant cells includes a coding region of a thionin gene, and a promoter region for transcribing the thionin gene to mRNA, and optionally an enhancer region for acting on the promoter to regulate the transcription activity thereof, and a terminator region for affecting the stability of the transcribed mRNA.

The present invention provides no limits as to the kind of promoter as long as it is capable of transcribing a thionin gene to mRNA within the plant cell into which the thionin gene is introduced. Such a promoter may be a promoter which is not derived from plants (e.g., a promoter for Cauliflower mosaic virus 35S (CaMV 35S) RNA, nopaline synthase (nos) or octopine synthase (ocs)), or a promoter which is derived from plants (e.g., a promoter for an enzyme involved in secondary metabolism such as a chalcone synthase or, a promoter for a storage protein such as glycinin). By appropriately selecting a promoter, it becomes possible to produce a plant exhibiting high disease resistance. An example of a preferable promoter for enabling thionin gene expression in a plant is a CaMV 35S promoter. The CaMV 35S promoter has been cloned in vectors such as pBI121 (Clontech), pBI221 (Clontech) and pCaMVCN (Pharmacia). In the present invention, the CaMV 35S promoter is preferably used in order to express a thionin gene in the cells of a transgenic plant.

The expression level of the introduced thionin gene can be enhanced by introducing an enhancer region. An enhancer region is a specific region within a non-translational region (e.g., intron) or a promoter region. An enhancer region can be disposed at the 5' and/or 3' of the promoter region to be employed. Examples of enhancer regions include: a region from −343 to −90 within the CaMV 35S promoter (Kar, R. et al., Science, 236: 1299–1302, 1987); 5' non-translational region of tobacco mosaic virus known as an Ω sequence (Gallie, D. R. et al., Nucl. Acids. Res., 15: 3257–3272, 1987); 5' non-translational region of alfalfa mosaic virus (Jobling, S. A. et al., Nature, 325: 622–625, 1987); and an intron sequence for phaseolin from Phaseolus vulgaris (Slightom, J. L. et al., Proc. Natl. Acad. Sci. USA 80: 1897–1901, 1983). Such an enhancer region may used alone or in combination with one another.

Furthermore, a plurality of these enhancer regions may be employed. In the present invention, the Ω sequence from tobacco mosaic virus, a region within the CaMV 35S promoter, or the intron sequence for phaseolin from *Phaseolus vulgaris* can be preferably used; more preferably, a combination of all of them is used. In the case of using such enhancer sequences in combination with the CaMV 35S promoter, preferably, the Ω sequence and the intron sequence for phaseolin from Phaseolus vulgaris are disposed at the 3' of the core region (−90 to −1) of the CaMV 35S promoter, while the enhancer region within the CaMV 35S promoter is disposed at the 5' of the core region (−90 to −1) of the CaMV 35S promoter. The number of enhancer sequences to be used depends on the plant to be transformed.

The expressed amount (translated amount) of thionin depends on the 3' non-translational region (i.e., terminator) located at the 3' of the thionin gene. By introducing a terminator including a polyadenylated signal site at the 3' of a coding region, the transcribed mRNA is stabilized so as to change the translated amount of thionin. Examples of such terminators include, without limitation, the CaMV 35S terminator, the terminator for nopaline synthase (nos terminator), and the terminator for octopine synthase (ocs terminator). In the present invention, the nos terminator is preferably used.

The thionin expression vector used in the present invention includes not only the thionin gene but also a gene which confers characteristics that serve as a selectable marker for facilitating the selection of the transformed plant cells (or plant). Such genes may be, for example, a neomycin phosphotransferase (NPTII) gene for conferring resistance against both antibiotics of kanamycin and neomycin, and a hygromycin phosphotransferase (HPT) gene for conferring resistance against hygromycin. Such a selectable marker gene can be used alone; alternatively, two or more of such selectable marker genes can be used in combination. In the present invention, the thionin expression vector preferably includes the NPTII gene and the HPT gene as selectable marker genes. These genes are also under the regulation of the CaMV 35S promoter, and include a nos terminator at their 3'. The resultant transgenic plants are conferred resistance against both kanamycin and neomycin.

The thionin expression vector used in the present invention may further include, if necessary: a region for enabling the incorporation of a region containing a thionin gene capable of stable expression within a plant cell and a selectable marker gene into the chromosomes of a plant cell (e.g., an RB sequence region and an LB sequence region from a Ti plasmid, which are involved in the induction of tumors due to infection of the soil bacterium *Agrobacterium tumefaciens*); and a region required for the replication within *Agrobacterium tumefaciens*. *Agrobacterium tumefaciens* is used for introducing the expression vector into a plant cell.

Furthermore, such an expression vector may include a gene region for replication in *E. coli* and a marker (e.g., ampicillin resistance) gene region for enabling subsequent selection in order to facilitate the gene recombinating operation on this vector. The expression vector used in the present invention preferably includes a thionin gene, drug resistance gene for facilitating selection, RB sequence and LB sequence region for enabling incorporation into the chromosomes of a plant cell, a region required for the replication within *Agrobacterium tumefaciens*, a gene region for replication in *E. coli* and a marker gene region for enabling subsequent selection.

Such an expression vector can be constructed by using an expression vector for plants containing the above regions, e.g., pBI121 (Clontech) from the Ti plasmid. pBI121 (Clontech) includes two expression units, namely, the P-glucuronidase (GUS) gene and the NPTII gene (which are respectively under the regulation of the CaMV 35S promoter and nos promoter), within a region interposed between an LB sequence and an RB sequence.

A thionin expression vector to be used in the present invention can be obtained by, for example, replacing a GUS region in pBI121 (Clontech) with a thionin coding region. In short, such an expression vector can be constructed by inserting a thionin coding region (obtained through digestion with restriction enzymes BamHI and SacI) into pBI121 (Clontech) from which the GUS region has been removed by digestion with restriction enzymes BamHI and SacI. An enhancer sequence can be obtained from, for example, $pL_{11}A$-A25 (Nishiguchi, M. et al., Nucl. Acids Res., 13: 5585–5590, 1985) and the aforementioned pBI121 (Clontech) after digestion with restriction enzymes, or by polymerase chain reaction (PCR) using the above vectors as templates with the use of an appropriate primer. Thereafter, these sequences can be introduced, for example, at the 5' of the CaMV 35S promoter by using the HindIII site, and/or at the 3' of the CaMV 35S promoter by using the BamHI site.

Alternatively, a specific portion of the necessary regions (e.g., a promoter region including an enhancer region, a region combining a coding region, and a promoter region and/or a terminator region, or a portion of such a region) in a thionin expression vector to be used in the present invention can be constructed on another cloning vector (e.g., pUC18 and pBluescript™ (Stratagene)). By introducing such a partial region into a expression vector for a plant cell (e.g., pBI121 (Clontech)) by replacement or the like, a thionin expression vector of interest, which is to be introduced into a plant cell, can be finally constructed. The method for constructing such an expression vector is not limited to that described above, but may vary within the knowledge of those skilled in the art.

The introduction of a constructed thionin expression cassette in a thionin expression vector can be accomplished by using a method using a soil bacterium having infection capabilities for plants, e.g., *Agrobacterium tumefaciens* or *Agrobacterium rizogenes*, a method using electroporation, or the like.

A method using *Agrobacterium tumefaciens* requires introduction of a constructed expression vector into *Agrobacterium tumefaciens* prior to infecting a plant cell therewith. The introduction of the constructed vector into *Agrobacterium tumefaciens* is performed by methods similar to those applied to *E. coli*, e.g., introduction by calcium treatment, a freezing and thawing method, or an electroporation method. Culturing of *Agrobacterium tumefaciens* into which the constructed vector is to be introduced can be performed under appropriate conditions (e.g., 25–30° C. for 24–36 hours) by using a medium such as LB medium or YEB medium.

The introduction of an expression vector into a plant cell through infection with *Agrobacterium tumefaciens* can be accomplished by allowing a seed or a tissue piece (e.g., a piece of a leaf and/or stem) of a plant to contact with *Agrobacterium tumefaciens* (in the form of bacteria or a culture solution thereof) containing the expression vector for a predetermined period of time. A method using a leaf piece is known to those skilled in the art as a leaf disk method (e.g., Horsch, R. B. et al., Science 227: 1229, 1985). The infection range and infection efficiency for the plants infectable with *Agrobacterium tumefaciens* depends on each strain. For example, the *Agrobacterium tumefaciens* strain LBA4404 easily infects a dicotyledon, especially tobacco, but hardly infects a monocotyledon such as rice. On the other hand, the *Agrobacterium tumefaciens* strain EHA101 has a sufficiently high infection efficiency for monocotyledons as compared with that of the strain LBA4404.

In order to ensure infection with *Agrobacterium tumefaciens*, the plant seed or tissue piece is placed on a solid medium after infection therewith. A combination of cytokinin and auxin is added to this medium for differentiation/induction and growth of the plant cell into a plant body. As cytokinin, for example, kinetin, benzyladenine, zeatin, or 2-isopentenyladenine is usually used at a concentration of 0.1–10 parts per million (ppm). As auxin, for example, indoleacetic acid, indolebutyric acid, 2-naphthaleneacetic acid, or 2,4-dichlorophenoxyacetic acid is usually used at a concentration of 1–10 ppm. The combination of these substances and their respective concentration levels vary depending on the plant and its tissue to be used, but those skilled in the art can determine such parameters by referring to experimental manuals (mentioned below) or the like.

Specifically, a culture solution of *Agrobacterium tumefaciens* (e.g., strain EHA 101) containing the expression vector and a callus obtained by culturing a seed are mixed and gently stirred (e.g., 15 minutes (min.)). Thereafter, in order to differentiate/induce the callus into a plant body, for example, the callus is placed on the agar medium of a plant tissue culturing medium (e.g., Murashige and Skoog's (MS) medium, Linsmaier and Skoog's (LS) medium, or Gamborg's B5 medium) to which 2,4-dichlorophenoxyacetic acid and sugar (usually 3% sucrose) have been added, and thereafter cultured for 3 days at 27° C., for example. It will be appreciated by those skilled in the art that the composition of the medium to be used varies depending on the plant and its tissue to be transformed.

Thereafter, selection of the infected cells containing the thionin gene is performed, concurrently with removal of *Agrobacterium tumefaciens* used for infecting the cells.

The removal of *Agrobacterium tumefaciens* is achieved as follows. The aforementioned callus is cultured on a medium obtained by further adding an antibiotics (e.g., 500 ppm carbenicillin or the like) to the aforementioned solid medium. The selection of the callus having the expression vector incorporated therein takes place on a medium to which antibiotics corresponding to the selectable marker genes present in the expression vector are added. For example, in the case where the callus are kanamycin or hygromycin resistant, 100 ppm kanamycin or 30 ppm hygromycin is used, respectively.

The callus are transferred onto a new selection medium every 2 or 3 weeks for removal of the bacterium and selection of the callus, as well as differentiation/induction of adventive buds. In order to ensure complete removal of *Agrobacterium tumefaciens*, carbenicillin may be further added at an early stage of culture on the selection medium. The culture temperature is usually between 20° C. and 30° C. A typically employed light/darkness condition is 16 hours of a light period and 8 hours of a darkness period. It will be appreciated by those skilled in the art that the culture condition varies depending on the plant.

Each adventive bud which has formed is extracted, transferred to a selection medium containing neither auxin nor cytokinin, and continued to culture under the same conditions as above until rooting. The plantlet thus obtained is acclimated so that it becomes capable of growing in a normal soil in a natural or artificial environment.

In another embodiment of the present invention, the introduction of an expression cassette including a thionin gene into a plant cell (infection) can be achieved by using a protoplast prepared from a plant tissue (e.g., a leaf) (e.g., Marton, L. et al, Nature, 277: 1229, 1979), instead of a seed. In the case of using a protoplast, an expression vector including a thionin gene can even be directly introduced into a plant cell by electroporation, if desired. The protoplast into which the expression vector has been introduced is cultured under appropriate conditions for regenerating cell walls. The subsequent procedure for differentiation/induction of the plant is the same procedure as that used in the above description of callus obtained from seeds.

Such a procedure for plant transformation is described in experimental manuals, e.g., Plant Genetic Transformation and Gene Expression A Laboratory Manual (Draper, J. et al.(Ed.), Blackwell Scientific Publications, 1988) and DNA Cloning, a practical approach (Glover, D. M. et al.(Ed.), vol.2, IRL Press, 1985).

The gene introduced into a transgenic plant according to the present invention can be subjected to qualitative and quantitative analyses by the following method.

For example, mRNA is recovered by a method including collecting plant leaves into which a thionin gene has been introduced, freezing the leaves in liquid nitrogen, and homogenating the leaves (Verwoerd et al., Nucl. Acids Res., 17: 2362, 1989). The analyses for the expression of the introduced thionin gene can be performed through a Northern blot analysis, where the recovered mRNA is separated by electrophoresis, transferred onto a nitrocellulose membrane or the like, and allowed to react with a labelled DNA or RNA probe which specifically hybridizes to the mRNA of the thionin gene. It will be appreciated by those skilled in the art that the recovery method of mRNA and the conditions for Northern blot analysis can be varied depending on the context of the present invention.

Alternatively, the analyses for the production of thionin may be performed by a Western blot analysis, where protein is recovered from transgenic plants by a known method, separated by electrophoresis, transferred onto a nitrocellulose membrane or the like, and allowed to bind to an antibody specific for a thionin, thereby the antibody is detected by using a labelled antibody ($^{125}$I-labelled antibody, or peroxidase-conjugated anti-IgG antibody) specific for that antibody. The qualitative and quantitative analyses of the gene introduced into a transgenic plant according to the present invention are not limited to those accomplished by the above-described methods.

The disease resistance of a transgenic plant according to the present invention can be determined as follows.

For example, leaves of a resultant transgenic plant are scarred with a needle or a knife (Mock treatment), where it is inoculated with a solution containing a pathogenic microbe. The area of the portion which has been damaged by the infection is compared against that of a wild type plant which has been subjected to the same treatment, thereby determining the resistance of the transgenic plant. It will be appreciated by those skilled in the art that the assay conditions may vary depending on the kind of plant to be examined and/or on the kind of pathogenic microbe used. Upon the assay, the comparison can be further facilitated by staining the tissue or cell, in a fixed or living state, with a dye such as aniline blue (Eschrich W. and Currier H. B., Stain Technology, 39: 303–307, 1964).

Alternatively, seeds obtained from a transgenic plant are immersed in a solution containing a pathogenic microbe before being sown over a soil, followed by being germinated and grown. Then the number of plants which undergo normal growth may be compared against the number of plants which undergo normal growth from the seeds of a wild type plant which has been subjected to the same treatment, thereby determining the resistance of the transgenic plant.

Alternatively, transformed plant cells and non-transformed plant cells may be cultured in a medium to which a pathogenic microbe has been added for a predetermined period (e.g., 3 days) and the number of surviving individuals may be compared, thereby determining the resistance of the transgenic plant.

It will be appreciated by those skilled in the art that the assay method for the disease resistance of the transgenic plant according to the present invention is not limited to those described above.

The transgenic plant according to the present invention is capable of forming seeds for propagation through cross-breeding (e.g., selfpollination, pollination between transgenic plants, or pollination between a transgenic plant and a wild type plant).

Furthermore, using the above described differentiation/induction procedure for obtaining a plant body from a infected cell, it is possible to obtain further transgenic plant bodies through culturing the tissues (e.g., root, stem or leaves) or organs (e.g., growing point or pollen) of the transgenic plant, not via the usual reproduction process (i.e., seeds). Such techniques and procedures are known to those skilled in the art. General methods for tissue culture are described in various experimental manuals.

The transgenic plant according to the present invention obtained as described above undergoes normal growth, without being impeded by the thionin gene introduced via transformation, and yet exhibits high resistance to at least one disease due to the expression of the thionin gene. Furthermore, the seeds from the transgenic plant according to the present invention also normally germinate and grow to exhibit high resistance to at least one disease. This indicates that the introduced thionin gene is retained in progenies, so that the disease resistance is stably passed onto the progenies. Accordingly, the present invention provides a practical and useful plant exhibiting high disease resistance.

Hereinafter, the present invention will be described by way of specific examples; however, the present invention is not limited to such examples.

EXAMPLE 1

Production of a transgenic rice (cv. Chiyohonami)

(1) Preparation of a thionin gene

A thionin gene was obtained by PCR using a cDNA clone of a thionin gene designated LTH92 (Japanese Laid-open Publication No. 8-266279, supra) and one pair of primers, in which additional restriction sites for BamHI and SacI were respectively added to each end of a thionin cDNA. The primers had the sequences shown as SEQ ID NOs: 1 and 2 which were synthesized based on conserved regions (5 region and acidic protein region) of a known thionin base sequence:

forward primer: 5'-AATCAAGCTTCCAAGTAG-AAGGCAAGAGTTGC-3'(SEQ ID NO: 1)
reverse primer:5'-AGTCTCTAGAGTCCA-TGTTGTCACAGACGG-3'(SEQ ID NO: 2)

A system containing 0.5 micro liter ($\mu$l) of Taq polymerase (5 unit per milli liter (U/ml)), 5 $\mu$l of 10× buffer (100 milli molar (mM) Tris (pH 8.3), 500 mM KCl, 1% Tritonx 100), 4 $\mu$l of 2.5 mM $MgCl_2$, 4 $\mu$l of 10 mM dNTPs, 1.25 $\mu$l of each of the above primers (10 pico mol (pmol)), and about 500 nano gram (ng) of cDNA, and brought up to 50 $\mu$l with distilled water, was used as the PCR reaction system. The reaction conditions of the PCR were as follows: After a single denaturing reaction for 2 minutes at 94° C., a reaction cycle was repeated 25 times, the reaction cycle comprising a denaturing reaction for 1 minute at 94° C.; an annealing reaction for 1 minute at 50° C.; and an extension reaction for 2 minutes at 72° C. Finally, an additional extension reaction was conducted for 5 minutes at 72° C.

(2) Construction of a thionin expression cassette and a thionin expression vector A promoter cassette portion was obtained by digesting pE7133GUS (Mitsuhara I. et al., Plant Cell Physiol., 37(1): 49–59, 1996) with restriction enzymes HindIII and BamHI, separating through agarose electrophoresis, and using Gene Clean II (BIO 101). A vector portion was obtained by digesting pBI121 (Clontech) with restriction enzymes HindIII and BamHI, separating through agarose electrophoresis, and using Gene Clean II (BIO 101). These portions were ligated by using a Takara Ligation Kit (Takara Shuzo Co., Ltd.) to obtain pBE7133GUS.

Next, pFF19 (Timmermans, M. C. P. et al., J. Biotechnol., 14: 333–344, 1990) was digested with restriction enzymes BamHI and SacI to isolate a hygromycin phosphotransferase (HPT) gene including a CaMV 35S promoter and a CaMV 35S terminator. After treating the resultant HPT gene fragment so as to have blunt ends, a SmaI linker was ligated to the blunt ended fragment. Then the resultant HPT gene fragment was digested with a restriction enzyme, Cfr9I, which is an isoschizomer of SmaI. Thereafter, this HPT gene fragment was inserted at the Cfr9I site located at the 3' of the GUS gene in pBE7133GUS, thereby obtaining pBE7133GUS-HPT.

Next, pBE7133GUS-HPT was digested with restriction enzymes BamHI and SacI to remove the GUS coding region, and the thionin gene obtained as described above was inserted to obtain a thionin expression vector pBE7133H-Thionin. A portion within pBE7133H-Thionin that extends from the CaMV 35S promoter (for regulating the NPTII gene) to the nos terminator (located at the 3' end of the HPT gene) and contains the thionin gene between the promoter and the terminator is defined as a thionin expression cassette.

(3) Introduction of the thionin expression cassette into *Agrobacterium tumefaciens* strain EHA101

*Agrobacterium tumefaciens* strain EHA101 (E. Hood et al., Journal of Bacteriology, 168(3): 1291–1301, 1986) was cultured with shaking overnight in 5 milli liter (ml) of YEB medium (0.1% yeast extract, 0.5% broth, 0.5% peptone, 0.5% sucrose, 0.05% $MgSO_4.7H_2O$) at 30° C. Then, 5 ml of this culture was added to 200 ml of YEB medium in a 1-liter flask, and further cultured for 5 to 6 hours at 30° C.

The bacteria were collected by centrifugation at 4000 rpm for 5 minutes, and suspended in 100 ml of 10 mM Tris-HCl (pH 8.0). Another centrifugation was conducted on the suspension and the collected bacteria were suspended in 2 ml of YEB medium. In a microfuge tube, 200 $\mu$l of this suspension and 100 $\mu$l of a DNA solution containing 0.5 $\mu$g of pBE7133H-Thionin were mixed and frozen in a dry ice/ethanol bath for 5 minutes. Then, the mixture was thawed in a warm bath maintained at 37° C. and kept for 25 minutes.

Thereafter, 2 ml of YEB medium was added to the mixture, and the mixture was cultured with shaking at 30° C. for 1 hour. A hundred $\mu$l of the culture was applied on YEB medium containing kanamycin (50 $\mu$g/ml) and hygromycin (50 $\mu$g/ml), and cultured at 30° C. for about 36 hours, whereby a resistant strain of *Agrobacterium tumefaciens* strain EHA101 was obtained.

The thionin expression cassette in the *Agrobacterium tumefaciens* strain EHA101 was isolated by an alkaline-SDS method; the existence and structure thereof were confirmed by a restriction enzyme analysis.

(4) Transformation of rice

Sterilized rice seeds were cultured at 27° C. for 2 weeks on MS medium (Murashige T. et al., Physiol. Plant., 15: 473, 1962) containing 2 milli gram per milli liter (mg/ml) of 2,4-dichlorophenoxyacetic acid (hereinafter referred to as "2,4-D"), whereby callus formed. The callus was transferred onto a cocultivation medium (i.e., an MS medium containing 2 mg/ml of 2,4-D and 1 g/l of casamino acid), and cultured at 27° C.

On the third day of culture, *Agrobacterium tumefaciens* strain EHA101 including the above-described thionin expression cassette was allowed to proliferate in YEB medium containing kanamycin and hygromycin, and centrifuged. After suspending pellets of bacteria in LB medium, acetosyringone was added to the suspension, thereby preparing a solution containing *Agrobacterium tumefaciens* strain EHA101 solution for infection. This bacterial solution was incubated at 30° C. for 20 minutes.

The aforementioned callus was added to the solution containing *Agrobacterium tumefaciens* strain EHA101 for infection on the fourth day of culture, and gently stirred for 15 minutes at 30° C., thereby allowing the callus to be infected. After stirring for 15 min., the callus was collected and placed on a cocultivation medium. The callus was cultured for 3 days with 16 hours of light per day at 27° C., and cultured on LB medium containing carbenicillin at 30° C. for 1 hour. Thereafter, only the callus was collected and placed on a selection (growth) medium (i.e., a cocultivation medium containing 500 mg/l of carbenicillin and 50 mg/l of hygromycin). The callus was cultured at 27° C. for 2 weeks with 16 hours of light per day.

The newly grown pale-yellow callus was transferred onto a selection (pretreatment-before-redifferentiation) medium (i.e., an N6 medium containing 1 mg/l of 2,4-D, 0.5 mg/l of BAP, 2 g/l of casamino acid, 20 g/l of sucrose, 30 g/l of sorbitol, 500 mg/l of carbenicillin, and 100 mg/l of hygromycin), and cultured for about 2 weeks. Thereafter, the callus was transferred onto a selection (redifferentiation) medium (i.e., an N6 medium containing 0.01 mg/i of r-naphthaleneacetic acid (NAA), 0.1 mg/l of BAP, 1 g/l of casamino acid, 500 mg/l of carbenicillin, and 100 mg/l of hygromycin). As a result, redifferentiated transgenic rice plants were obtained in about 2 to 3 weeks.

EXAMPLE 2

Resistance assay for rice (cv. Chiyohonami) against bacterial leaf blight of rice The resistance assay against bacterial leaf blight of rice was conducted by using the leaves from the first generations of selfed plants (named line 2-1, line 11-2, and line 13-3) of transgenic rice obtained through selection using hygromycin as well as the leaves of a wild type rice. The rice leaves were scarred in two points with a short needle, and inoculated with a bacterium causing bacterial leaf blight of rice (i.e., *Xanthomonas campestris* pv. *oryzae*) by using a bacterial suspension containing $1 \times 10^7$ cfu/ml of bacterium causing bacterial leaf blight of rice. After 2 weeks of cultivation, the areas of the respective leaves which were damaged through infection with the bacterium causing bacterial leaf blight of rice were visibly evaluated. As an index of resistance against bacterial leaf blight of rice, a disease index of bacterial leaf blight of rice based on leaf blade needle inoculation by Noda et al. ("HOKURIKU NOUSHI HOUKOKU" 1989) was used.

The wild type rice, which had been inoculated with the bacterium causing bacterial leaf blight of rice, had an disease index of 4.4, whereas line 2-1, line 11-2, and line 13-3 of the first generations of selfed plants of transgenic rice, which had been inoculated with the bacterium causing bacterial leaf blight of rice, had disease indices of 1.8, 0.8 and 2.2 respectively. Thus, the transgenic rice showed a high disease resistance against bacterial leaf blight of rice.

Figure 1:
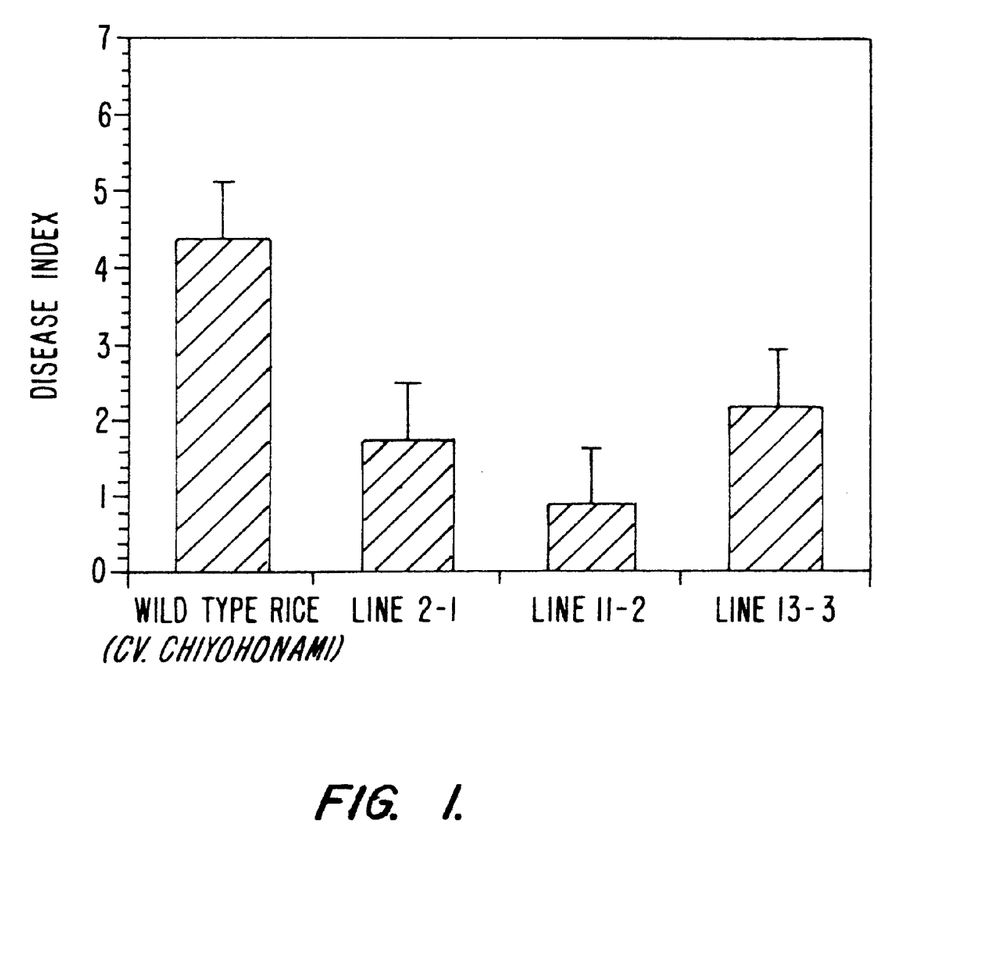
FIG. 1 is a graph illustrating the resistances of some transgenic rice lines (2-1, 11-2 and 13-3) against bacterial leaf blight of rice based on their disease indices, where a thionin gene has been introduced into each of the transgenic rice.
Figure 2:
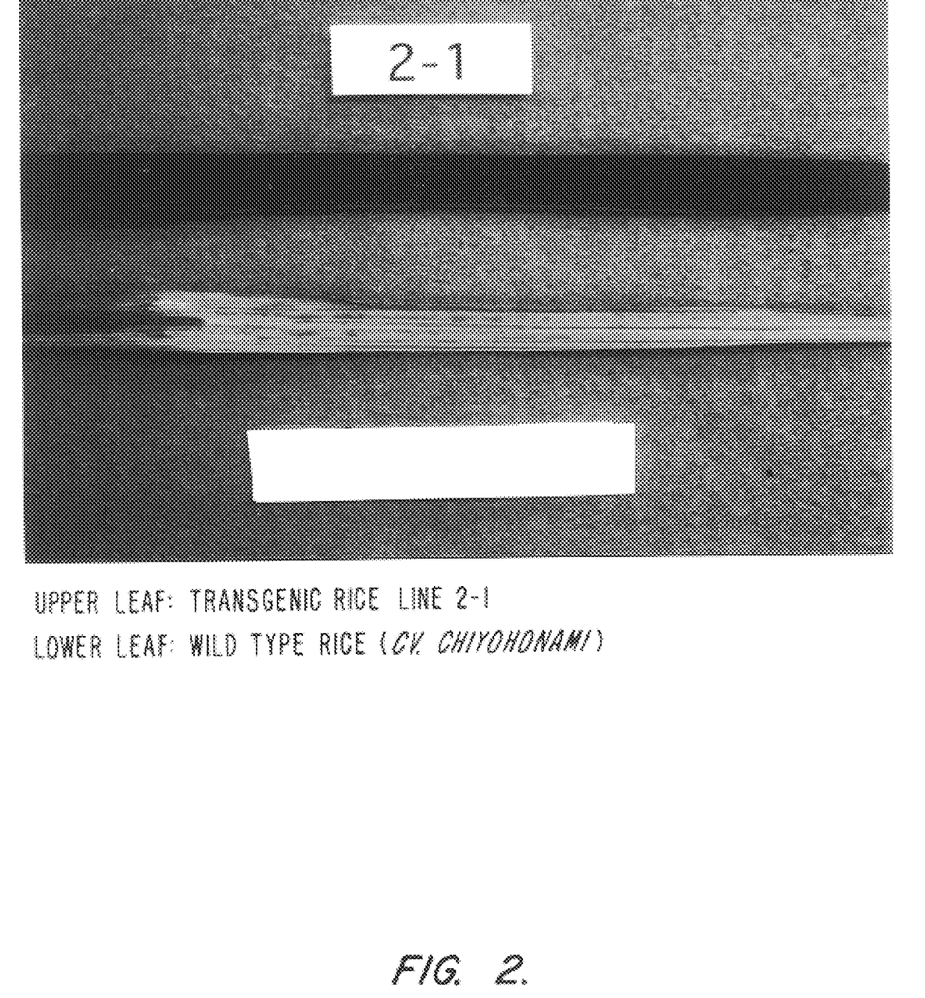
FIG. 2 is a photograph showing the results of the resistance assay for the transgenic rice line 2-1 against bacterial leaf blight of rice, where a thionin gene has been introduced into the transgenic rice line 2-1.

The results are shown in FIGS. 1 and 2.

FIG. 1 is a graph illustrating resistance against bacterial leaf blight of rice based on disease indices of bacterial leaf blight of rice. Eight leaves were assayed for each individual to determine its disease index of bacterial leaf blight of rice, and an average value thereof is shown in the graph.

FIG. 2 is a photograph showing the results of the resistance assay. The upper leaf is a leaf from the first generation of selfed plant line 2-1 of transgenic rice inoculated with the bacterium causing bacterial leaf blight of rice, whereas the lower leaf is a leaf from a wild type rice inoculated with the bacterium causing bacterial leaf blight of rice.

EXAMPLE 3

Resistance assay for rice (cv. Chiyohonami) against bacterial seedling blight of rice The resistance assay against bacterial seedling blight of rice was conducted by using the seeds from the second generations of selfed plants (named line 2-1.1 and line 11-2.1) of transgenic rice as well as the seeds from a wild type rice. The rice seeds were subjected to suction in a suspension containing $1 \times 10^6$ cfu/ml of bacterium causing bacterial seedling blight of rice (i.e., *Pseudomonas plantari*) for 1 hour, immersed therein for 3 hours, and air dried overnight at room temperature. Immersion of seeds was effected at 20° C. for 3 days in a double amount of ion exchanged water, and germination was forced for 1 day at 37° C. under high humidity conditions. Thereafter, the seeds were sown (24 seeds/minicup) over a soil for breeding paddy rice. The germination was allowed for 3 days under high humidity and darkness conditions at 30° C., and thereafter seedlings were cultivated in a closed greenhouse. The resistance was assayed about 10 days from sowing by comparing the number of individuals which undergo normal growth from these seeds as well as the rate of seedling establishment.

In the case where the seeds from the wild type rice were infected with the bacterium causing bacterial seedling blight of rice, all the individuals withered soon after germination. On the other hand, in the case where the seeds from the second generation of selfed plant line 2-1.1 of transgenic rice was infected with the bacterium causing bacterial seedling blight of rice, the seeds which were sown showed a seedling establishment rate of 75% and underwent normal growth. Also in the case where the second generation of selfed plant line 11-2.1 of transgenic rice, the seeds which were sown showed a seedling establishment rate of 96% and similarly under-went normal growth. Thus, the transgenic rice showed a high disease resistance against bacterial seedling blight of rice.

Figure 3:
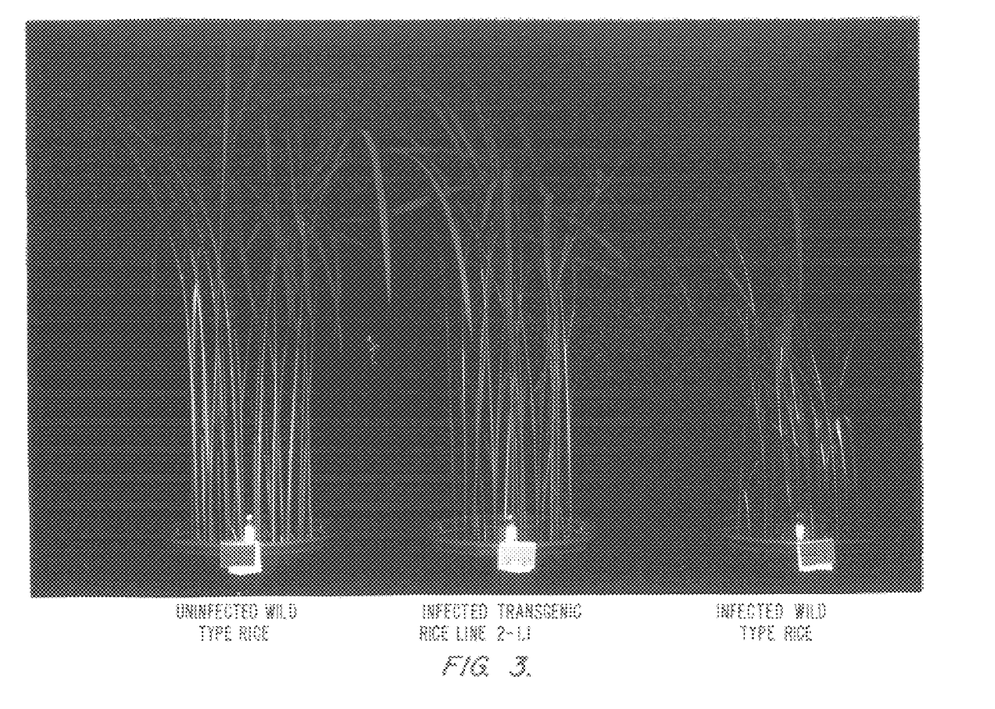
FIG. 3 is a photograph showing the results of the resistance assay for the transgenic rice line 2-1.1 against bacterial seedling blight of rice, where a thionin gene has been introduced into the transgenic rice line 2-1.1. The plant on the left (positive control) is a wild type rice which was not inoculated with the bacterium causing bacterial seedling blight of rice; the plant in the middle is a transgenic rice line 2-1.1 which was inoculated with the bacterium causing bacterial seedling blight of rice; and the plant on the right (negative control) is a wild type rice which was inoculated with the bacterium causing bacterial seedling blight of rice.

The results are shown in Table 1 and FIG. 3.

FIG. 3 is a photograph showing the results of the resistance assay. The plant on the left (positive control) is a wild type rice which was not inoculated with the bacterium causing bacterial seedling blight of rice; the plant in the middle is a transgenic rice line 2-1.1 which was inoculated with the bacterium causing bacterial seedling blight of rice; and the plant on the right (negative control) is a wild type rice which was inoculated with the bacterium causing bacterial seedling blight of rice.

TABLE 1

Resistance of the transgenic rice expressing the thionin against bacterial seedling blight of rice

| | line | state of germination | | | rate of seedling establishment |
| --- | --- | --- | --- | --- | --- |
| | | normal | withered | ungerminated | |
| uninoculated | wild type rice | 22 | 2 | 0 | 92% |
| inoculated | wild type rice | 0 | 22 | 2 | 0% |
| | 2–1.1 | 18 | 4 | 2 | 75% |
| | 11–2.1 | 23 | 1 | 0 | 96% |

EXAMPLE 4

Production of transgenic tobacco (*Nicotiana tabacum* Sammsun NN)

A thionin gene was prepared, and a thionin expression cassette and a thionin expression vector were constructed in the same manner as described in Example 1.

(1) Introduction of a thionin expression cassette into *Agrobacterium tumefaciens* strain LBA4404

*Agrobacterium tumefaciens* strain LBA4404 (Clontech) was cultured at 28° C. in LB medium (10 g/l bactotriptone, 5 g/l of yeast extract, 10 g/l of NaCl (pH 7.2)) containing 250 pg/ml of streptomycin and 50 µg/ml of rifampicin. A bacterial suspension of *Agrobacterium tumefaciens* strain LBA4404 was prepared following the method of Nagel et al. (Microbiol. Lett., 67, 325 (1990)), and the thionin expression vector pBE7133H-Thionin prepared in Example 1 (2) was introduced in this bacterium strain by electroporation.

The thionin expression cassette within *Agrobacterium tumefaciens* strain LBA4404 was isolated by an alkaline-SDS method; the existence and structure thereof were confirmed by a restriction enzyme analysis.

(2) Transformation of tobacco

*Agrobacterium tumefaciens* strain LBA4404 including the thionin expression cassette obtained as described above was cultured with shaking overnight in YEB medium at 28° C. A leaf which had completely extended from a tobacco plant was cut off and sterilized. The sterilized leaf was cut with a paper punch, thereby making a leaf disk.

The leaf disk was immersed in the aforementioned culture medium solution (diluted 20× with sterilized water) and was allowed to gently permeate for 1 to 2 minutes. After permeation, the leaf disk was cultured in MS medium at 27° C. for 2 days. After culturing, the leaf disk was transferred onto MS agar medium containing carbenicillin, and cultured under illumination at 26° C. for 1 week, thereby removing *Agrobacterium tumefaciens* strain LBA4404 from the leaf disk.

The leaf disk from which *Agrobacterium tumefaciens* strain LBA4404 had been removed was subcultured every 2 weeks on an MS agar medium containing carbenicillin, kanamycin and hygromycin, and a transformed leaf disk was selected. A callus was induced from this transformed leaf disk by an ordinary method, and redifferentiated into a tobacco plant body.

EXAMPLE 5

Resistance assay for tobacco (*Nicotiana tabacum* Sammsun NN) against late blight of potato The resistance assay against late blight of potato was conducted by using the leaves from the transgenic tobaccos (named lines 4, 5, 15, 18, 41 and 44) obtained as described above as well as the leaves from a wild type tobacco. A fungus causing late blight of potato (i.e., *Phytophthora infestans*) was cultured on PDA medium (Tifco) at 18° C. to 20° C. for about 1 week, and the resultant colonies were punched out with a cork bowler (diameter: 3 mm), thereby preparing fungus causing late blight of potato agar blocks. The agar block was placed on the above leaf in such a manner that the colony and the leaf were in contact with each other, thereby allowing the leaf to be inoculated with the fungus causing late blight of potato, and maintained at 27° C. After 2 or 3 days, the area of the diseased spots on the leaf was visibly evaluated.

The diseased spot area on the leaf from the wild type tobacco inoculated with the fungus causing late blight of potato was 976 mm$^2$. The diseased spot area on the leaf from the transgenic tobacco inoculated with the fungus causing late blight of potato was 48 mm$^2$ for line 4, 57 mm$^2$ for line 44, and 40 mm$^2$ for line 18. Furthermore, lines 5, 15 and 41 received substantially no damage from the fungus causing late blight of potato. Thus, the transgenic tobacco showed a high disease resistance against late blight of potato.

Figure 4:
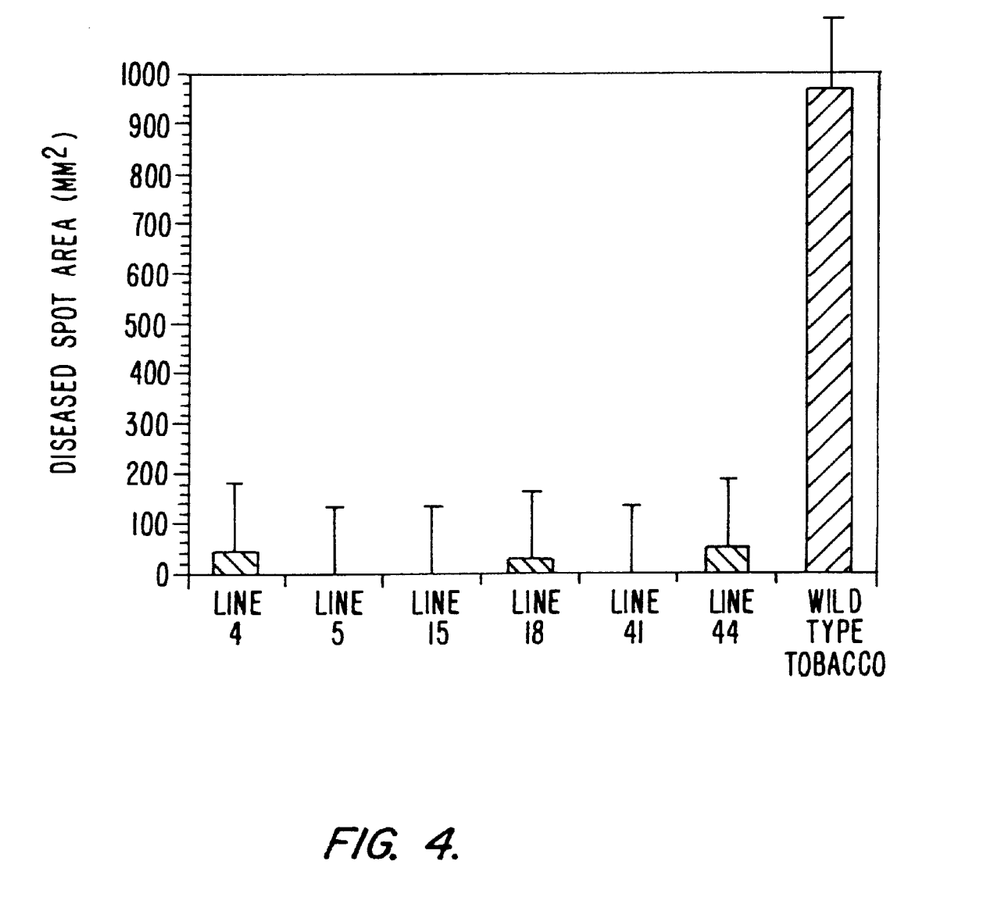
FIG. 4 is a graph illustrating the resistances of the transgenic tobacco lines (4, 5, 15, 18, 41 and 44) against the late blight of potato based on their diseased spot areas, where a thionin gene has been introduced into each of the transgenic tobaccos.
Figure 5:
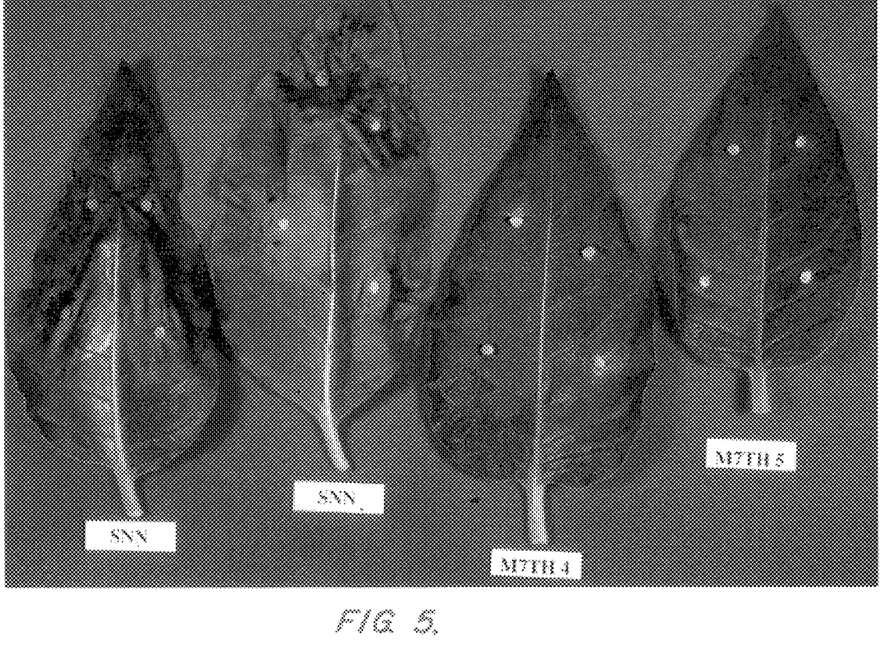
FIG. 5 is a photograph showing the results of the resistance assay for the transgenic tobacco lines (M7TH4 and M7TH5) against the late blight of potato, where a thionin gene has been introduced into each of the transgenic tobaccos.

The results are shown in FIGS. 4 and 5.

FIG. 4 is a graph illustrating resistance against late blight of potato based on diseased spot area. Four points were examined on the leave from each individual, and an average value of the diseased spot area due to the fungus causing late blight of potato is shown in the graph.

FIG. 5 is a photograph showing the results of the resistance assay, illustrating the states of the respective individuals 3 days after the inoculation with the fungus causing late blight of potato. The two leaves on the left are leaves from a wild type tobacco inoculated with the fungus causing late blight of potato, whereas the two leaves on the right are respective leaves from transgenic tobacco lines 4 (M7TH4) and 5 (M7TH5) inoculated with the fungus causing late blight of potato.

According to the present invention, there is provided a transgenic plant which exhibits resistance to at least one disease, and generally a plurality of diseases, the transgenic plant being obtained by introducing a gene encoding thionin, which is an antimicrobial protein. A method for producing such a plant is also provided by the present invention. The present invention can impart a number of high quality plant species which have conventionally been susceptible to diseases with a high disease resistance, thereby facilitating stable production of high quality plant species. The improved disease resistance also makes it possible to reduce the reliance on agricultural chemicals for exterminating pathogenic microbes. Thus, the present invention greatly contributes to agricultural production.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. A method for producing a transgenic plant, comprising the steps of:
   constructing an expression vector comprising an expression cassette comprising a thionin gene from *Avena sativa*, the expression cassette expressing the thionin gene;
   transforming a plant cell with the expression vector to produce a transformed plant cell; and
   regenerating the transgenic plant from the tranformed plant cell;
   wherein the transgenic plant has enhanced resistance to at least one disease compared to non-transgenic plants, wherein the disease is a disease caused by a plant pathogenic bacterium, wherein the disease is bacterial leaf blight of rice or bacterial seedling blight of rice, and wherein the transgenic plant is a plant of the family Poaceae.

2. A method for producing a transgenic plant, comprising the steps of:

constructing an expression vector comprising an expression cassette comprising a thionin gene from *Avena sativa*, the expression cassette expressing the thionin gene;

transforming a plant cell with the expression vector to produce a transformed plant cell; and regenerating the transgenic plant from the transformed plant cell;

wherein the transgenic plant has enhanced resistance to at least one disease compared to non-transgenic plants, wherein the disease is a disease caused by a plant pathogenic filamentous fungus, wherein the disease is late blight of potato and wherein the transgenic plant is a plant of the family Solanaceae.

3. A method for conferring resistance to at least one disease to a plant, comprising the steps of:

transforming a plant cell with an expression vector which comprises an expression cassette comprising a thionin gene from *Avena sativa*, the expression cassette expressing the thionin gene to produce a transformed plant cell; and regenerating a transgenic plant from the transformed plant cell;

wherein the transgenic plant has enhanced resistance to at least one disease compared to non-transgenic plants, wherein the disease is a disease caused by a plant pathogenic bacterium, wherein the disease is bacterial leaf blight of rice or bacterial seedling blight of rice, and wherein the transgenic plant is a plant of the family Poaceae.

4. A method for conferring resistance to at least one disease to a plant, comprising the steps of:

transforming a plant cell with an expression vector which comprises an expression cassette comprising a thionin gene from *Avena sativa*, the expression cassette expressing the thionin gene to produce a transformed plant cell; and regenerating a transgenic plant from the transformed plant cell, wherein the transgenic plant has enhanced resistance to at least one disease compared to non-transgenic plants, wherein the disease is a disease caused by a plant pathogenic filamentous fungus wherein the disease is late blight of potato, and wherein the transgenic plant is a plant of the family Solanaceae.

* * * * *

SEQUENCE LISTING

<160> NUMBER OF SEQ ID NOS: 2

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence:primer

<400> SEQUENCE: 1
aatcaagctt ccaagtagaa ggcaagagtt gc                32

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence:primer

```
-continued

<400> SEQUENCE: 2
agtctctaga gtccatgttg tcacagacgg                                            30
```